United States Patent [19]

Dudek et al.

[11] 4,012,228

[45] Mar. 15, 1977

[54] LOW INTRINSIC VALUE ALLOYS

[75] Inventors: Ronald P. Dudek, River Grove; Peter Kosmos, Alsip; John A. Tesk, Woodridge, all of Ill.

[73] Assignee: Howmedica, Inc., New York, N.Y.

[22] Filed: May 14, 1976

[21] Appl. No.: 686,346

[52] U.S. Cl. ............................ 75/134 C; 75/134 T; 75/165; 75/153; 75/172 R; 75/172 G

[51] Int. Cl.² ......................................... C22C 30/00

[58] Field of Search ......... 75/134 C, 134 N, 134 T, 75/165, 172 R, 172 G, 153

[56] References Cited

UNITED STATES PATENTS

| | | | |
|---|---|---|---|
| 2,050,040 | 8/1936 | Coleman et al. | 75/134 C |
| 2,050,077 | 8/1936 | Wise | 75/134 C |
| 2,216,495 | 10/1940 | Loebich | 75/165 |
| 2,270,594 | 1/1942 | Leuser | 75/134 N |
| 2,460,595 | 2/1949 | Reich | 75/134 C |
| 2,597,495 | 5/1952 | Jackson et al. | 75/171 |
| 3,134,671 | 5/1964 | Prosen | 75/172 G |
| 3,574,611 | 4/1971 | Prosen | 75/165 |
| 3,819,366 | 6/1974 | Katz | 75/172 R |
| 3,841,868 | 10/1974 | Dudek et al. | 75/171 |
| 3,892,564 | 7/1975 | Hatswell et al. | 75/165 |

*Primary Examiner*—L. Dewayne Rutledge
*Assistant Examiner*—E. L. Weise
*Attorney, Agent, or Firm*—Francis X. Murphy; Charles J. Knuth; Allen J. Spiegel

[57] ABSTRACT

A low intrinsic value alloy for dental and jewelry use includes the following ranges of constituents in percentages by weight:

| Constituents | Proportional Range |
|---|---|
| Gold | 0–45% |
| Platinum | 0–30% |
| Palladium | 0–20% |
| Copper | 30–55% |
| Gallium | 5–10% |
| Zinc | 0–1% |
| Iridium | 0–0.01% | with the proviso that the total of said gold, platinum and palladium is at least about 35%.

7 Claims, No Drawings

LOW INTRINSIC VALUE ALLOYS

Background of the Invention

This invention relates to alloys. More specifically it relates to low intrinsic value alloys for use in the construction of dental restorations such as inlays, crowns, bridges and partial dentures. It is also useful in producing lower cost jewelry.

Due to the variety of applications encountered in dental crown and bridge work, the need for alloys having specific values of hardness and strength has been recognized as evidenced by the American Dental Association (ADA) Specification No. 5 which defines four basic alloy types.

Current gold-colored dental crown and bridge alloys are typically gold based with additions of platinum, palladium, silver, copper, zinc, and other base metals and are characteristically higher in intrinsic value than alloys of this invention. Currently employed gold-colored alloys owe their high intrinsic value primarily to the relatively high levels of gold, platinum and palladium which are necessary to instill the required tarnish and corrosion resistance. Recently, there has been a trend toward a reduction in the noble metal content of these alloys to lower their intrinsic value.

U.S. Pat. No. 3,892,564 discloses gallium-bearing gold alloys, particularly low melting point alloys, useful as solders for articles of jewelry and in dental work, and containing apart from impurities, 1–10 wt. percent gallium, 0–25 wt. percent copper, 0–33 wt. percent silver and 0–10 wt. percent zinc, the balance in all cases consisting of gold. Specifically disclosed is an alloy containing 10% gallium, 15% copper and 75% gold.

SUMMARY OF THE INVENTION

It has now been discovered that a low intrinsic value alloy for dental and jewelry use, possessing mechanical and physical properties similar to those gold casting alloys in current use, can be achieved by incorporating the following ranges of constituents in percentages by weight:

| Constituents | Proportional Range |
| --- | --- |
| Gold | 0–45% |
| Platinum | 0–30% |
| Palladium | 0–20% |
| Copper | 30–55% |
| Gallium | 5–10% |
| Zinc | 0–1% |
| Iridium | 0–0.01% |

With the proviso that the total of said gold, platinum and palladium is at least about 35%.

DETAILED DESCRIPTION OF THE INVENTION

The relative proportions of the various elements comprising the alloy composition of the invention have been determined as the result of intensive investigation to obtain an alloy composition having optimum chemical and physical properties. Specifically, we have found that the alloy composition of the invention should contain by weight gold 0–45%, platinum 0–30%, palladium 0–20%, copper 30–55%, gallium 5–10%, zinc 0–1% and iridium 0–0.01% with the proviso that the total of said gold, platinum and palladium is at least about 35%. Preferred alloy compositions are those which contain about 10% gallium, gold 15–30%, platinum 0–20%, palladium 5–20%, copper 40–45% and iridium 0–0.01%; and gold 30–45%, platinum 0–10%, palladium 0–20%, copper 35–45%, gallium 5–10%, zinc 0–1% and iridium 0–0.01%.

Particular examples of the alloys of this invention are listed below in Examples 1–30 giving especially preferred compositions in percentages by weight. They have been categorized by their respective ADA type numbers as indicated only by their hardness values. These alloys include a group of gold-colored alloys of low intrinsic value which have been found particularly useful in the construction of dental restorations such as inlays, crowns, bridges and partial dentures. They are also used in producing lower cost jewelry.

Alloys of this invention have the following advantages when compared to alloys of the lower intrinsic value, such as the nickel-chromium base dental alloys disclosed in U.S. Pat. Nos. 3,841,868 and 2,597,495, which are now being marketed as substitutes for the ADA certified dental gold casting alloys: lower casting temperature and handling characteristics similar to higher nobel metal content alloys; and gold color but with low gold and noble metal content.

Also, the alloy system described in this invention possesses the necessary latitude in terms of hardness and strength to satisfy the variety of requirements demanded by the dental profession in crown and bridge work. This point is significant in that current alloys of lower intrinsic values have characteristically been of higher hardness value and were therefore unfit for use as inlays and low stress restorations where alloys of low hardness are required.

These alloys, although designed for use in dental crown and bridge work could also find use in the jewelry industry where their good gold color and tarnish and corrosion resistance would also be desirable in producing lower cost jewelry.

The alloys described in this invention have been designed to possess hardness and strength values within the ranges indicated in the American Dental Association Specification No. 5 for Dental Casting Gold Alloys for Type I, Type II, Type III and Type IV alloys.

Not all compositions in the invention alloy range will produce alloys which are gold in color. However, those which are not gold-colored are still suitable for dentistry and jewelry, due to their high corrosion and tarnish resistance and low intrinsic value owing to their relatively low noble metal content.

The role of each of the respective alloying elements is believed to be as follows:

Gold: Noble metal addition which improves the corrosion and tarnish resistance of the alloy and contributes to the "gold" color of the alloy.

Platinium: Noble metal addition which improves the corrosion and tarnish resistance of the alloy and also acts as a hardening agent to control the hardness and strength of the alloy to specified values.

Palladium: Noble metal addition which improves the corrosion and tarnish resistance of the alloy and also acts as a hardening agent to control the alloy's hardness and strength to specified values.

Copper: Base metal addition which contributes to the "gold" color of the alloys and also acts as a hardening agent to increase the hardness and strength of the alloy.

Gallium: Base metal addition which improves the corrosion and tarnish resistance of the alloy. The addition of gallium also acts to enhance the gold color of the alloy by interacting in a way to lessen the red-rose hue typical of similar copper-containing alloys without gallium. Gallium additions also have the effect of lowering the hardness of the alloys as compared to similar alloys not containing gallium. Gallium additions also lower the melting point of the alloy system to improve castability.

Zinc: Base metal addition which acts as deoxidizer, and also lowers the melting point of the alloy system to improve castability.

Iridium: Precious metal addition used as a grain refiner.

The following specific properties were determined in the manner described below:

Hardness

Equipment — Rockwell Hardness tester

Test specimen — cast piece one half × three fourths × one eighth inch thick.

Test method — the hardness numbers were determined in the following three states, and converted to Brinell values:

1. As Cast Condition
2. Annealed — quenched after heating for 10 minutes at 1290° F.
3. Heat treated as per American Dental Association Specification No. 5.

Sag Temperature

Equipment — Muffle furnace with two point support stand having 1 inch span

Test specimen — cast piece 1¼ inches long, ¾ inch wide and 0.030–0.040 inch thick Test method — Support stand preheated to within 200° F. of anticipated sag temperature. Specimen is placed on stand and allowed to equilibrate. The temperature is then raised in 20° increments until sag is visually observed.

The following examples are merely illustrative and in no way limit the scope of the claims.

Examples 1–7 are Type I Dental Casting Gold Alloys ADA Specification No. 5. Hardness 45–75 Bhn (Quenched).

EXAMPLE 1

| Constituent | Composition |
| --- | --- |
| Gold | 40% |
| Platinum | 7.49% |
| Palladium | 5% |
| Copper | 37.5% |
| Gallium | 10% |
| Iridium | 0.01% |
| Hardness Values (Bhn) | |
| As Cast | 65 |
| Quenched | 58 |
| ADA Heat Treated | 67 |
| Sag Temperature | 1520–1540° F |

EXAMPLE 2

| Constituent | Composition |
| --- | --- |
| Gold | 40% |
| Platinum | 4.99% |
| Palladium | 7.5% |
| Copper | 37.5% |
| Gallium | 10% |
| Iridium | 0.01% |
| Hardness Values (Bhn) | |
| As Cast | 74 |
| Quenched | 62 |

EXAMPLE 2-continued

| Constituent | Composition |
| --- | --- |
| ADA Heat Treated | 78 |
| Sag Temperature | 1520–1540° F |

EXAMPLE 3

| Constituent | Composition |
| --- | --- |
| Gold | 40% |
| Platinum | 7.49% |
| Palladium | 7.5% |
| Copper | 35% |
| Gallium | 10% |
| Iridium | 0.01% |
| Hardness Values (Bhn) | |
| As Cast | 101 |
| Quenched | 71 |
| ADA Heat Treated | 235 |
| Sag Temperature | 1500–1520° F |

EXAMPLE 4

| Constituent | Composition |
| --- | --- |
| Gold | 40% |
| Platinum | 4.99% |
| Palladium | 5% |
| Copper | 40% |
| Gallium | 10% |
| Iridium | 0.01% |
| Hardness Values (Bhn) | |
| As Cast | 76 |
| Quenched | 69 |
| ADA Heat Treated | 73 |
| Sag Temperature | 1460–1480° F |

EXAMPLE 5

| Constituent | Composition |
| --- | --- |
| Gold | 45% |
| Platinum | 7.49% |
| Palladium | 7.5% |
| Copper | 30% |
| Gallium | 10% |
| Iridium | 0.01% |
| Hardness Values (Bhn) | |
| As Cast | 256 |
| Quenched | 72 |
| ADA Heat Treated | 210 |
| Sag Temperature | 1420–1440° F |

EXAMPLE 6

| Constituent | Composition |
| --- | --- |
| Gold | 35% |
| Platinum | 19.99% |
| Copper | 35% |
| Gallium | 10% |
| Iridium | 0.01% |
| Hardness Values (Bhn) | |
| As Cast | 200 |
| Quenched | 66 |
| ADA Heat Treated | 179 |
| Sag Temperature | 1500–1520° F |

EXAMPLE 7

| Constituent | Composition |
| --- | --- |
| Gold | 25% |
| Platinum | 19.99% |
| Palladium | 5% |
| Copper | 40% |
| Gallium | 10% |
| Iridium | 0.01% |
| Hardness Values (Bhn) | |
| As Cast | 165 |
| Quenched | 75 |
| ADA Heat Treated | 162 |
| Sag Temperature | 1580–1600° F |

Examples 8–14 are Type II Dental Casting Gold Alloys ADA Specification No. 5. Hardness 70–100 Bhn (Quenched).

EXAMPLE 8

| Constituent | Composition |
| --- | --- |
| Gold | 20% |
| Platinum | 15% |
| Palladium | 10% |
| Copper | 45% |
| Gallium | 10% |
| Hardness Values (Bhn) | |
| As Cast | 121 |
| Quenched | 92 |
| ADA Heat Treated | 106 |
| Sag Temperature | 1660–1680° F |

EXAMPLE 9

| Constituent | Composition |
| --- | --- |
| Gold | 35% |
| Platinum | 9.99% |
| Palladium | 5% |
| Copper | 40% |
| Gallium | 10% |
| Iridium | 0.01% |
| Hardness Values (Bhn) | |
| As Cast | 107 |
| Quenched | 82 |
| ADA Heat Treated | 106 |
| Sag Temperature | 1580–1600° F |

EXAMPLE 10

| Constituent | Composition |
| --- | --- |
| Gold | 35% |
| Platinum | 7.49% |
| Palladium | 7.5% |
| Copper | 40% |
| Gallium | 10% |
| Iridium | 0.01% |
| Hardness Values (Bhn) | |
| As Cast | 110 |
| Quenched | 90 |
| ADA Heat Treated | 123 |
| Sag Temperature | 1600–1620° F |

EXAMPLE 11

| Constituent | Composition |
| --- | --- |
| Gold | 35% |
| Platinum | 7.49% |
| Palladium | 7.5% |
| Copper | 42.5% |
| Gallium | 7.5% |
| Iridium | 0.01% |
| Hardness Values (Bhn) | |
| As Cast | 127 |
| Quenched | 93 |
| ADA Heat Treated | 114 |
| Sag Temperature | 1600–1680° F |

EXAMPLE 12

| Constituent | Composition |
| --- | --- |
| Gold | 35% |
| Platinum | 7.49% |
| Palladium | 7.5% |
| Copper | 39.5% |
| Gallium | 10% |
| Iridium | 0.01% |
| Zinc | 0.5% |
| Hardness Values (Bhn) | |
| As Cast | 119 |
| Quenched | 88 |
| ADA Heat Treated | 125 |
| Sag Temperature | ~1620–1640° F |

EXAMPLE 13

| Constituent | Composition |
| --- | --- |
| Gold | .45% |
| Platinum | 4.99% |
| Palladium | 5% |
| Copper | 40% |
| Gallium | 5% |
| Iridium | 0.01% |
| Hardness Values (Bhn) | |
| As Cast | 121 |
| Quenched | 88 |
| ADA Heat Treated | 117 |
| Sag Temperature | 1640–1660° F |

EXAMPLE 14

| Constituent | Composition |
| --- | --- |
| Gold | 35% |
| Platinum | 15% |
| Copper | 40% |
| Gallium | 10% |
| Hardness Values (Bhn) | |
| As Cast | 147 |
| Quenched | 83 |
| ADA Heat Treated | 106 |
| Sag Temperature | 1580–1600° F |

Examples 15–24 are Type III Alloys ADA Specification No. 5. Hardness 90–140 Bhn (Quenched).

EXAMPLE 15

| Constituent | Composition |
| --- | --- |
| Gold | 20% |
| Platinum | 20% |
| Palladium | 5% |
| Copper | 45% |
| Gallium | 10% |
| Hardness Values (Bhn) | |
| As Cast | 132 |
| Quenched | 101 |
| ADA Heat Treated | 116 |

EXAMPLE 15-continued

| Constituent | Composition |
|---|---|
| Sag Temperature | 1660–1680° F |

EXAMPLE 16

| Constituent | Composition |
|---|---|
| Platinum | 30% |
| Palladium | 5% |
| Copper | 55% |
| Gallium | 10% |
| Hardness Values (Bhn) | |
| As Cast | 153 |
| Quenched | 130 |
| ADA Heat Treated | 130 |
| Sag Temperature | 1900–1920° F |

EXAMPLE 17

| Constituent | Composition |
|---|---|
| Platinum | 25% |
| Palladium | 10% |
| Copper | 55% |
| Gallium | 10% |
| Hardness Values (Bhn) | |
| As Cast | 159 |
| Quenched | 132 |
| ADA Heat Treated | 139 |
| Sag Temperature | 1840–1860° F |

EXAMPLE 18

| Constituent | Composition |
|---|---|
| Platinum | 30% |
| Palladium | 10% |
| Copper | 50% |
| Gallium | 10% |
| Hardness Values (Bhn) | |
| As Cast | 139 |
| Quenched | 137 |
| ADA Heat Treated | 141 |
| Sag Temperature | 1840–1860° F |

EXAMPLE 19

| Constituent | Composition |
|---|---|
| Gold | 35% |
| Palladium | 15% |
| Copper | 40% |
| Gallium | 10% |
| Hardness Values (Bhn) | |
| As Cast | 242 |
| Quenched | 121 |
| ADA Heat Treated | 235 |
| Sag Temperature | 1600–1620° F |

EXAMPLE 20

| Constituent | Composition |
|---|---|
| Gold | 35% |
| Platinum | 0.09% |
| Palladium | 14.9% |
| Copper | 40% |
| Gallium | 10% |

EXAMPLE 20-continued

| Constituent | Composition |
|---|---|
| Iridium | 0.01% |
| Hardness Values (Bhn) | |
| As Cast | 200 |
| Quenched | 119 |
| ADA Heat Treated | 165 |
| Sag Temperature | 1580–1600° F |

EXAMPLE 21

| Constituent | Composition |
|---|---|
| Gold | 30% |
| Platinum | 9.99% |
| Palladium | 10% |
| Copper | 40% |
| Gallium | 10% |
| Iridium | 0.01% |
| Hardness Values (Bhn) | |
| As Cast | 179 |
| Quenched | 123 |
| ADA Heat Treated | 162 |
| Sag Temperature | 1640–1660° F |

EXAMPLE 22

| Constituent | Composition |
|---|---|
| Gold | 35% |
| Platinum | 7.49% |
| Palladium | 7.5% |
| Copper | 45% |
| Gallium | 5% |
| Iridium | 0.01% |
| Hardness Values (Bhn) | |
| As Cast | 147 |
| Quenched | 110 |
| ADA Heat Treated | 175 |
| Sag Temperature | 1680–1770° F |

EXAMPLE 23

| Constituent | Composition |
|---|---|
| Gold | 35% |
| Platinum | 7.49% |
| Palladium | 7.5% |
| Copper | 39% |
| Gallium | 10% |
| Zinc | 1% |
| Iridium | 0.01% |
| Hardness Values (Bhn) | |
| As Cast | 127 |
| Quenched | 93 |
| ADA Heat Treated | 125 |
| Sag Temperature | <1500° F |

EXAMPLE 24

| Constituent | Composition |
|---|---|
| Gold | 35% |
| Platinum | 7.49% |
| Palladium | 7.5% |
| Copper | 41.5% |
| Gallium | 7.5% |
| Zinc | 1% |
| Iridium | 0.01% |
| Hardness Values (Bhn) | |
| As Cast | 117 |
| Quenched | 92 |
| ADA Heat Treated | 123 |

EXAMPLE 24-continued

| Constituent | Composition |
|---|---|
| Sag Temperature | 1540–1560° F |

Examples 25–30 are Type IV Alloy ADA Specification No. 5. Hardness 130 Bhn, minimum (Quenched).

EXAMPLE 25

| Constituent | Composition |
|---|---|
| Gold | 20% |
| Platinum | 20% |
| Palladium | 10% |
| Copper | 40% |
| Gallium | 10% |
| Hardness Values (Bhn) | |
| As Cast | 228 |
| Quenched | 185 |
| ADA Heat Treated | 222 |
| Sag Temperature | 1660–1680° F |

EXAMPLE 26

| Constituent | Composition |
|---|---|
| Gold | 35% |
| Platinum | 10% |
| Palladium | 10% |
| Copper | 35% |
| Gallium | 10% |
| Hardness Values (Bhn) | |
| As Cast | 263 |
| Quenched | 153 |
| ADA Heat Treated | 249 |
| Sag Temperature | 1580–1600° F |

EXAMPLE 27

| Constituent | Composition |
|---|---|
| Gold | 30% |
| Platinum | 0.09% |
| Palladium | 19.9% |
| Copper | 40% |
| Gallium | 10% |
| Iridium | 0.01% |
| Hardness Values (Bhn) | |
| As Cast | 276 |
| Quenched | 176 |
| ADA Heat Treated | 276 |
| Sag Temperature | 1600–1620° F |

EXAMPLE 28

| Constituent | Composition |
|---|---|
| Gold | 25% |
| Platinum | 4.99% |
| Palladium | 20% |
| Copper | 40% |
| Gallium | 10% |
| Iridium | 0.01% |
| Hardness Values (Bhn) | |
| As Cast | 270 |
| Quenched | 200 |
| ADA Heat Treated | 263 |
| Sag Temperature | 1660–1680° F |

EXAMPLE 29

| Constituent | Composition |
|---|---|
| Gold | 20% |
| Platinum | 9.99% |
| Palladium | 20% |
| Copper | 40% |
| Gallium | 10% |
| Iridium | 0.01% |
| Hardness Values (Bhn) | |
| As Cast | 256 |
| Quenched | 228 |
| ADA Heat Treated | 242 |
| Sag Temperature | 1680–1700° F |

EXAMPLE 30

| Constituent | Composition |
|---|---|
| Gold | 15% |
| Platinum | 14.99% |
| Palladium | 20% |
| Copper | 40% |
| Gallium | 10% |
| Iridium | 0.01% |
| Hardness Values (Bhn) | |
| As Cast | 263 |
| Quenched | 228 |
| ADA Heat Treated | 228 |
| Sag Temperature | 1700–1720° F |

What is claimed is:

1. An alloy consisting essentially of the following constituents in the indicated percentages by weight:

| Constituents | Proportional Range |
|---|---|
| Gold | 0–45% |
| Platinum | 0–30% |
| Palladium | 0–20% |
| Copper | 30–55% |
| Gallium | 5–10% |
| Zinc | 0–1% |
| Iridium | 0–0.01% | with the proviso that the total of said gold, platinum and palladium is at least about 35%.

2. An alloy in accordance with claim 1 containing about 10% gallium and the following additional constituents in the indicated ranges of percentages by weight:

| Constituent | Proportional Range |
|---|---|
| Gold | 15–30% |
| Platinum | 0–20% |
| Palladium | 5–20% |
| Copper | 40–45% |
| Iridium | 0–0.01% |

3. The alloy of claim 2 consisting of the following constituents in approximately the indicated percentages by weight:

| Constituent | Proportional Range |
|---|---|
| Gold | 25% |
| Platinum | 19.99% |
| Palladium | 5% |

4. An alloy in accordance with claim 1 containing the following constituents in the indicated ranges of percentages by weight:

| Constituent | Proportional Range |
|---|---|
| Gold | 30–45% |
| Platinum | 0–10% |
| Palladium | 0–20% |
| Copper | 35–45% |
| Gallium | 5–10% |
| Zinc | 0–1% |
| Iridium | 0–0.01% |

5. The alloy of claim 4 consisting of the following constituents in approximately the indicated percentages by weight:

| Constituent | Proportional Range |
|---|---|
| Gold | 45% |
| Platinum | 4.99% |
| Palladium | 5% |
| Copper | 40% |
| Gallium | 5% |

| Constituent | Proportional Range |
|---|---|
| Iridium | 0.01% |

6. The alloy of claim 4 consisting of the following constituents in approximately the indicated percentages by weight:

| Constituent | Proportional Range |
|---|---|
| Gold | 35% |
| Platinum | 0.09% |
| Palladium | 14.9% |
| Copper | 40% |
| Gallium | 10% |
| Iridium | 0.01% |

7. The alloy of claim 4 consisting of the following constituents in approximately the indicated percentages by weight:

| Constituent | Proportional Range |
|---|---|
| Gold | 35% |
| Platinum | 10% |
| Palladium | 10% |
| Copper | 35% |
| Gallium | 10% |

* * * * *